United States Patent
Keenan et al.

(10) Patent No.: US 6,255,262 B1
(45) Date of Patent: Jul. 3, 2001

(54) HIGH HYDROXYL CONTENT GLYCEROL DI-ESTERS

(75) Inventors: Michael J. Keenan, Baton Rouge, LA (US); Martin A. Krevalis, The Maxwell (SG); David W. Turner, Baton Rouge, LA (US)

(73) Assignee: Exxon Chemical Patents Inc., Houston, TX (US)

( * ) Notice: Subject to any disclaimer, the term of this patent is extended or adjusted under 35 U.S.C. 154(b) by 0 days.

(21) Appl. No.: 09/188,849

(22) Filed: Nov. 9, 1998

(51) Int. Cl.[7] .................................................. C10M 105/38
(52) U.S. Cl. .................... 508/486; 508/487; 508/495; 508/308; 252/68; 560/180
(58) Field of Search ...................................... 508/308, 384, 508/485, 495, 486, 487; 252/68; 560/180, 181

(56) References Cited

U.S. PATENT DOCUMENTS

| | | |
|---|---|---|
| 2,523,309 * | 9/1950 | Kester . |
| 3,579,548 * | 5/1971 | Whyte ................................ 508/486 |
| 4,234,498 | 11/1980 | Lok . |
| 5,538,654 * | 7/1996 | Lawate et al. ....................... 508/486 |
| 5,665,686 | 9/1997 | Schlosberg et al. . |

FOREIGN PATENT DOCUMENTS

| | | | |
|---|---|---|---|
| 0178913 | 4/1986 | (EP) | .............................. C07C/69/28 |
| 739 970 | 10/1996 | (EP) . | |
| WO 93/22270 | 11/1993 | (WO) . | |
| 9628525 | 9/1996 | (WO) | ......................... C10M/105/40 |

OTHER PUBLICATIONS

Glydexx® Glycidyl Esters, Jun. 1994 USA.

* cited by examiner

Primary Examiner—Margaret Medley

(57) ABSTRACT

A process for reproducibly forming a thermally and oxidatively stable high hydroxyl glycerol di-ester compound which is particularly useful as a lubricant. The glycerol di-ester compound is formed by reacting a glycidyl ester with an excess of a neo acid salt. The di-ester product is produced in a nearly quantitative conversion and is readily recoverable from the reaction mixture via a water wash, vacuum dry, and a mild wiped film evaporator treatment.

22 Claims, No Drawings

HIGH HYDROXYL CONTENT GLYCEROL DI-ESTERS

The present invention relates to a glycerol di-ester compounds and a method for making the same. In particular, such high hydroxyl content polyol ester compounds are useful as lubricants for synthetic passenger car engine oils.

BACKGROUND OF THE INVENTION

Lubricants in commercial use today are prepared from a variety of natural and synthetic base stocks which are admixed with various additive packages and solvents depending upon the intended use of the lubricant. Conventional base stocks include, for example, mineral oils, highly refined mineral oils, poly alpha olefins (PAO), polyalkylene glycols (PAG), phosphate esters, silicone oils, and polyol esters.

Lubricants are oftentimes used under extreme thermal and oxidative conditions, such as in aircraft turbines and in internal combustion engines. Polyol esters have been commonly used as lubricating base stocks in automobile and aircraft engine oils. The inherent thermal and oxidative stability of polyol esters is relatively high compared to other base stocks (e.g., mineral oils, poly alpha olefins, and the like). However, even these synthetic esters lubricants are subject to oxidative degradation and cannot be used for long periods of time under oxidizing conditions without further modification. It is known that this degradation is related to the oxidation and hydrolysis of the ester base stock. Such deterioration is manifested by the formation of products of oxidation such as sludge and varnish like deposits on the metal surface, and by viscosity and acidity growth.

Conventional synthetic polyol ester engine and turbine oil formulations require the addition of anti-oxidants (also known as oxidation inhibitors). Such anti-oxidants include arylamines (e.g. dioctyl phenylamine and phenylalpha-naphthylamine), and the like. Anti-oxidants reduce the tendency of the ester base stock to deteriorate. Upon thermal oxidative stress, a weak carbon-hydrogen bond is cleaved resulting in a unstable carbon radical of the ester. The role of conventional antioxidants is to transfer a hydrogen atom to the unstable ester radical and effect a "healing" of the radical. The following equation demonstrates the effect of the antioxidant (AH):

$$AH + ROO \cdot \rightarrow A \cdot + ROOH$$

The anti-oxidant molecule is converted into a radical, but this radical (A.) is far more stable that that of the ester based system. Thus, the effective lifetime of the ester is extended. When the added anti-oxidant is consumed, the ester radicals are not healed and oxidative degradation of the polyol ester composition occurs.

Frequently replacing the lubricating oil or adding an antioxidant thereto to suppress oxidation increases the cost of maintaining internal combustion engines and aircraft turbines. It would be desirable to have an ester base stock which exhibits substantially enhanced thermal and oxidative stability compared to conventional synthetic ester base stocks, and wherein the ester base stock does not require frequent replacement due to decomposition (i.e., oxidative degradation). It would be economically desirable to eliminate the amount of antioxidant which is normally added to such lubricant base stocks.

U.S. Pat. No. 5,665,686, which is incorporated herein by reference, describes high hydroxyl content polyol esters that are useful as lubricants since the highly branched polyol ester backbone permits the high hydroxyl ester to act in a manner similar to an anti-oxidant. The high hydroxyl content causes the thermal and oxidative stability of a polyol ester to drastically increase as measured by high pressure differential scanning calorimetry (HPDSC) by providing an intermolecular mechanism which is capable of scavenging alkoxyl and alkyl peroxides, thereby reducing the rate at which oxidation degradation occurs as compared to similar, low hydroxyl content polyol esters.

In addition, U.S. Pat. No. 5,665,686 also discloses that high hydroxyl content polyol esters exhibit lower friction coefficients and wear volume than fully esterified polyol esters.

The present invention provides a method for producing glycerol di-esters which can be used as a base stock lubricant. The present method is unique since it can quantitatively produce an essentially pure di-ester with virtually no mono-esters or trimesters. Previously, such di-esters were produced in combination with mono-esters and tri-esters by, for example, the acid esterification of glycerol as disclosed in EP 0 739 970 A1.

The thermal and oxidative stability of the di-ester compound of the present invention eliminates or reduces the level of anti-oxidant which must be added to a lubricant, thereby providing a substantial cost savings.

Also, since the method of the present invention produces essentially pure di-esters, the reproducibility and consistency of the lubricant is greatly enhanced compared to mixtures of polyol esters where the esterification process results in varying concentrations of mono-esters, di-esters and trimesters. The important anti-oxidant hydroxyl content of the polyol ester mixtures produced by the acid-alcohol esterification process will be much more varied than the essentially pure di-ester.

Furthermore, the reaction conditions of the present invention are mild compared to the alcohol-acid esterification process. The alcohol-acid esterification process requires a reaction temperature of over 100° C., and typically over 200° C., wherein the present reaction method only requires temperatures of about 70° to 90° C.

Moreover, the di-ester product is readily recoverable from the reaction mixture. Reactants not consumed in the process can be treated by a water washing, vacuum drying and a mild wiped film evaporator treatment. On the other hand, the alcohol-acid esterification isolation process is much more complicated and expensive. For example, if a catalyst is used in the alcohol-acid esterification, it is typically removed by filtering the reaction mixture and distilling the resulting filtrate. If it is difficult to remove the catalyst, a filter aid may be needed. Also, the unreacted alcohol (glycerol) may adversely affect the performance of the lubricant by deteriorating the anti-wear properties. Therefore, it is preferable to reduce the alcohol content of the reaction mixture by distillation which is expensive. Furthermore, it is unlikely that the unreacted alcohol can be removed completely by distillation. Thus, the method according to the present invention is much simpler, results in essentially a pure di-ester with no alcohol content, and is economically more efficient than the conventional alcohol-acid esterification process.

SUMMARY OF THE INVENTION

The present invention is directed to a thermal and oxidative stable glycerol di-ester compound which is useful as a lubricant having glycerol di-ester concentration of at least 80%, preferably 90%, and a hydroxyl number of between about 100 to 150, and most preferably a hydroxyl number between about 110 to 140. The glycerol di-ester compound is made by reacting a glycidyl ester with an excess of a neo acid salt. The di-ester product is produced in a nearly quantitative conversion and is readily recoverable via a water wash, vacuum dry, and/or a mild wiped film evaporator treatment which removes slight traces of any reactants. The present invention is further directed to a method of forming glycidyl di-esters by reacting a glycidyl ester and a metal salt of a neo acid.

DETAILED DESCRIPTION AND EMBODIMENTS OF THE INVENTION

The high hydroxyl glycerol di-ester compound of the present invention is formed by the step of reacting a glycidyl ester, or its chlorohydrin ester precursor, with an excess of a neo acid salt according to the equation immediately below:

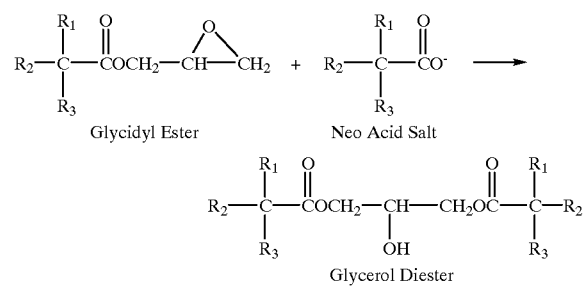

wherein $R_1$, $R_2$ and $R_3$ are linear, branched or cyclic alkyls group having one or more carbon atoms, preferably from 1 to 22 carbon atoms, or a linear, branched or cyclic alkenyl group having one or more carbon atoms, preferably from 1 to 22 carbon atoms. None of $R_1$, $R_2$ and $R_3$ can be hydrogen. The term "neo" acid, as used herein, refers to a trialkyl or trialklylene acetic acid, i.e., an acid which is triply substituted at the alpha carbon with alkyl or alkylene groups.

It has been found that reaction products of glycidyl ester with a stoichiometric excess (about 1.05 to 1.3 moles) of the neo acid salt at about 70° to about 90° C. for about 5 to about 8 hours results in nearly quantitative conversion of the glycidyl ester to the glycerol di-ester.

The glycidyl ester can be produced by reacting a chlorohydrin ester with an alkaline metal hydroxide according to the following equation.

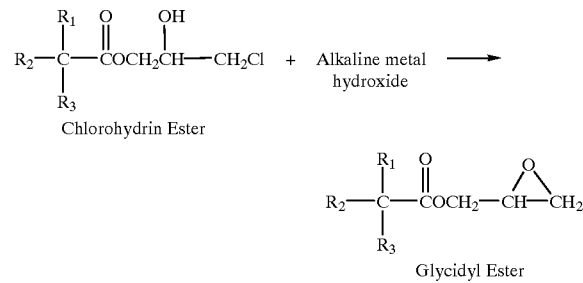

Any suitable alkaline metal hydroxide may be used in the reaction. Examples of suitable salts are NaOH, KOH, $Mg(OH)_2$, $Ca(OH)_2$, and the like. The preferred alkaline metal hydroxide is NaOH.

The chlorohydrin ester intermediate is produced by reacting a neo acid with epichlorohydrin in the presence of alkaline solution according to the following equation.

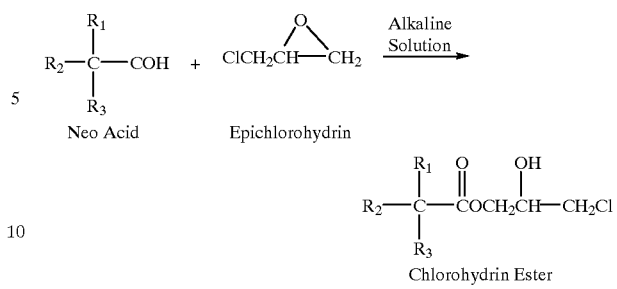

Any suitable alkaline solution may be used for this reaction. Examples of suitable solutions are solutions of NaOH, KOH, $Mg(OH)_2$, $Ca(OH)_2$, $N(CH_3)_4OH$, $N(CH3)_4HCl$, and the like, The preferred alkaline metal solution is a combination of NaOH and $(CH_3)_4NCl$.

The neo acids can be prepared by the reaction of an olefinic hydrocarbon cut with formic acid or alternatively with carbon monoxide and water in an acid catalyzed reaction as disclosed in WO 93122270, which is incorporated herein by reference.

Examples of the alkyl groups represented by $R_1$, $R_2$, and $R_3$ include, but are not limited to, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl nonyldecyl, eicosanyl, heneicossanyl, docosyl and the like.

The preferred carboxylic acids are 2,2-dimethyl propionic acid (neopentanoic acid), neoheptanoic acid, neooctantoic acid, neononanoic acid, neodecanoic acid, neoundecanoic acid, neododecanoic acid, and neotridecanoic acid.

The preferred hydroxyl number of the glycerol di-ester composition according to the present invention is between about 100 to 150, and most preferably about 110 to 140. For example, a di-neodecanoyl ester of glycerol has a molecular weight of 400 which gives 2.50 milliequivalents per gram of hydroxyl functionality for a theoretical hydroxyl number of 140.3. At 80% diester the hydroxyl number is about 112 and at 90% diester the hydroxyl number is about 126.

The glycerol di-ester compound of the present invention can be used in the formulation of various lubricants, such as, crankcase engine oils, (i.e., passenger car motor oils, heavy duty diesel motor oils, and passenger car diesel oils), two cycle engine oils, catapult oil, drilling fluids, aircraft and other turbine oils, greases, compressor oils, hydraulic fluids, gear oils, functional fluids and other industrial and engine lubrication applications.

Other constituents in the lubrication formulation may include auxiliary base stocks. The preferred auxiliary base stock constituents include mineral oils, highly refined mineral oils, poly alpha olefins, polyalkylene glycols, phosphate esters, silicone oils, and other polyol esters. The glycerol di-ester is blended with the auxiliary base stock in an amount between about 1% to about 50% by weight based on the total weight of the lubricant.

In addition, the lubrication formulation of the present invention may contain an additive package. The preferred additive package constituents include at least one of viscosity index improvers, corrosion inhibitors, oxidation inhibitors, dispersants, lube oil flow improvers, detergents, rust inhibitors, pour point depressants, anti-foaming agents, anti-wear agents, seal swellants, friction modifiers, extreme pressure agents, color stabilizers, demulsifiers, wetting agents, water loss improving agents, bactericides, drill bit lubricants, thickeners or gellants, anti-emulsifying agents, metal deactivators, and additive solubilizers.

In some of the lubricating formulations, a solvent may be added depending on the specific application. Examples of solvents include hydrocarbon solvents if such as toluene, benzene, xylene, and the like.

Optionally, an anti-oxidant is present in the lubrication in an amount ranging from between about 0% to 5% by weight based on the glycerol di-ester compound. More preferably, the anti-oxidant ranges from between about 0.01% to 2.5% by weight.

The formulated lubricant according to the present invention preferably comprises about 66–99% by weight of the glycercol ester of the present invention, about 1% to about 20% by weight of the additive package and about 0 to about 20% by weight of a solvent. The lubricant can also contain about 1% to about 50% by weight of the auxiliary basestock described previously.

The advantage of the glycerol di-ester in the lubricant is that the unconverted hydroxyl group results in greater thermal and oxidative stability compared to complex acid esters that are fully esterified. In addition, the reaction produces nearly quantitative conversions resulting in an essentially pure di-ester. Therefore, a lubricant containing the glycerol di-ester will have more consistent and reproducible thermal and oxidative properties than lubricants containing mixtures of esters produced by the conventional alcohol-acid esterification process which contain varying concentrations of the mono-esters, di-esters and trimesters. In addition, the high hydroxyl content of the glycerol di-ester exhibits lower fiction coefficients and wear volumes than fully substituted polyol esters, such that this unique present glycerol di-ester may be used as an anti-wear agent and/or friction modifier.

The process for producing the di-ester also has many advantages over the method for producing the mixture of esters. First, the present reaction is conducted under mild conditions with a reaction temperature in the range of about 70° to 90° C., compared to the conventional acid-alcohol esterification process in which the reaction temperature is typically greater than 200° C. Also, the glycerol di-ester compound is readily recoverable from the reaction mixture by water washing to remove the excess acid salt. The unreacted chlorohydrin/glycidyl esters may be removed by drying under vacuum and a mild wiped film evaporator treatment. The mild conditions and ease of isolation results in an cost efficient process.

While several embodiments in accordance with the invention have been shown and described, it is to be clearly understood that the same are susceptible to numerous changes apparent to one skilled in the art. Therefore, we do not wish to be limited to the details shown and described, but intend to show all changes and modifications that come within the scope of the appended claims.

What is claimed is:

1. A process for producing a glycerol di-ester composition comprising the steps of reacting a glycidyl ester having the formula:

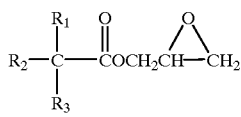

wherein $R_1$, $R_2$ and $R_3$ are independently linear, branched or cyclic alkyls having from 1 to 22 carbon atoms, or linear, branched or cyclic alkenyl groups having 1 to 22 carbon atoms;

with an excess of a neo acid salt, thereby forming said glycerol di-ester composition having a glycerol di-ester concentration of at least 80% and a hydroxyl number in the range between about 100 to 150.

2. The process of claim 1 wherein said glycidyl ester is produced by reacting a chlorohydrin ester with an alkaline metal salt.

3. The process of claim 2 wherein said alkaline metal salt is NaOH.

4. The process of claim 1 wherein said glycidyl ester is produced by reacting a neo acid with epichlorohydrin in the presence of alkaline solution.

5. The process of claim 4 wherein said alkaline solution comprises NaOH, and $(CH_3)_4NCl$.

6. The process of claim 4 wherein said neo acid is at least one acid selected from the group consisting of:
neopentanoic acid, neoheptanoic acid, neooctantoic acid, neononanoic acid, neodecanoic acid, neoundecanoic acid, neododecanoic acid, and neotridecanoic acid.

7. The process of claim 1 wherein said glycidyl ester and said neo acid salt are reacted at a temperature of from about 70° C. to 90° C.

8. The process of claim 1 wherein said glycidyl ester and said neo acid salt are reacted for a time of from about 5 hours to 8 hours.

9. The process of claim 1 further comprising the step of:
isolating the glycerol di-ester by washing, drying and evaporation.

10. A lubricant comprising:
a glycerol di-ester composition formed by reacting a glycidyl ester haying the formula:

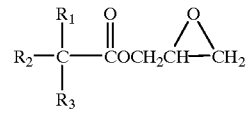

wherein $R_1$, $R_2$ and $R_3$ are independently linear, branched or cyclic alkyls having from 1 to 22 carbon atoms, or linear, branched or cyclic alkenyl groups having 1 to 22 carbon atoms;
with an excess of a neo acid salt, thereby forming said glycerol di-ester composition having a glycerol di-ester concentration of at least 80% and a hydroxyl number in the range between about 100 to 150; and
at least one additive.

11. The lubricant of claim 10 wherein said glycidyl ester is produced by reacting a chlorohydrin ester with an alkaline metal salt.

12. The lubricant of claim 11 wherein said alkaline metal salt is NaOH.

13. The lubricant of claim 12 wherein said glycidyl ester is produced by reacting a neo acid with epichlorohydrin in the presence of alkaline solution.

14. The lubricant of claim 13 wherein said alkaline solution comprises NaOH, and $(CH_3)_4NCl$.

15. The lubricant of claim 13 wherein said neo acid is at least one acid selected from the group consisting of: neopentanoic acid, neoheptanoic acid, neooctantoic acid, neononanoic acid, neodecanoic acid, neoundecanoic acid, neododecanoic acid, and neotridecanoic acid.

16. The lubricant of claim 10 wherein said glycidyl ester and said neo acid salt are reacted at a temperature of from about 70° C. to 90° C.

17. The lubricant of claim 10 wherein said glycidyl ester and said neo acid salt are reacted for a time of from about 5 hours to 8 hours.

18. The lubricant of claim 10 further formed by isolating the glycerol di-ester by washing, drying and evaporation.

19. The lubricant of claim 10 further comprising at least one auxiliary base stock selected from the group consisting of: mineral oils, highly refined mineral oils, poly alpha olefins, polyalkylene glycols, phosphate esters, silicone oils, di-esters, and polyol esters.

20. The lubricant of claim 10 wherein said additive is at least one selected from the group consisting of: viscosity index improvers, corrosion inhibitors, oxidation inhibitors, dispersants, lube oil flow improvers, detergents, rust inhibitors, pour point depressants, anti-foaming agents, anti-wear agents, seal swellants, friction modifiers, extreme pressure agents, color stabilizers, demulsifiers, wetting agents, water loss improving agents, bactericides, drill bit lubricants, thickeners or gellants, anti-emulsifying agents, metal deactivators, and additive solubilizers.

21. The lubricant of claim 10 further comprising a solvent.

22. The lubricant of claim 10 for use in at least one of the following applications: crankcase engine oils, two cycle engine oils, catapult oil, drilling fluids, aircraft and other turbine oils, greases, compressor oils, hydraulic fluids, gear oils, functional fluids and other industrial and engine lubrication applications.

* * * * *